US011072771B2

(12) United States Patent
Brutinel et al.

(10) Patent No.: US 11,072,771 B2
(45) Date of Patent: *Jul. 27, 2021

(54) SELF-CONTAINED ANAEROBIC CULTURE DEVICE WITH MICROCOMPARTMENTS

(71) Applicant: 3M INNOVATIVE PROPERTIES COMPANY, St. Paul, MN (US)

(72) Inventors: Evan D. Brutinel, Inver Grove Heights, MN (US); Jason W. Bjork, Cottage Grove, MN (US); Adam J. Stanenas, Cottage Grove, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 158 days.

This patent is subject to a terminal disclaimer.

(21) Appl. No.: 15/763,744

(22) PCT Filed: Sep. 27, 2016

(86) PCT No.: PCT/US2016/053863
§ 371 (c)(1),
(2) Date: Mar. 27, 2018

(87) PCT Pub. No.: WO2017/058737
PCT Pub. Date: Apr. 6, 2017

(65) Prior Publication Data
US 2018/0273887 A1    Sep. 27, 2018

Related U.S. Application Data

(60) Provisional application No. 62/233,567, filed on Sep. 28, 2015.

(51) Int. Cl.
| C12M 1/32 | (2006.01) |
| C12M 1/00 | (2006.01) |
| C12M 1/34 | (2006.01) |
| C12Q 1/04 | (2006.01) |
| C12Q 1/24 | (2006.01) |

(52) U.S. Cl.
CPC ............ *C12M 23/12* (2013.01); *C12M 23/38* (2013.01); *C12M 41/34* (2013.01); *C12M 41/36* (2013.01); *C12Q 1/04* (2013.01); *C12Q 1/24* (2013.01)

(58) Field of Classification Search
CPC ...................................................... C12Q 1/24
See application file for complete search history.

(56) References Cited

U.S. PATENT DOCUMENTS

| 3,338,794 A | 8/1967 | Bladel |
| 4,565,783 A | 1/1986 | Hansen |
| 4,656,783 A | 4/1987 | Ahonen |
| 5,089,413 A | 2/1992 | Nelson |
| 5,232,838 A | 8/1993 | Nelson |
| 5,518,892 A | 5/1996 | Naqui |
| 6,531,281 B1 | 3/2003 | Magot |
| 6,689,438 B2 | 2/2004 | Kennedy |
| 2011/0217728 A1 | 9/2011 | Yin |

FOREIGN PATENT DOCUMENTS

| CA | 2176895 | 11/1996 |
| CN | 1696306 | 11/2005 |
| CN | 102329851 | 9/2012 |
| GB | 1437404 | 5/1976 |
| JP | H05-013200 | 2/1993 |
| JP | H07-75545 | 3/1995 |
| JP | 2007-124985 | 5/2007 |
| WO | WO 1995-23026 | 8/1995 |
| WO | WO 2012-094603 | 7/2012 |
| WO | WO 2013-029106 | 3/2013 |
| WO | WO 2014-042933 | 3/2014 |
| WO | WO 2014-054494 | 4/2014 |
| WO | WO 2014-085333 | 6/2014 |
| WO | WO 2015-061213 | 4/2015 |
| WO | WO 2016-176176 | 11/2016 |

OTHER PUBLICATIONS

Dragavon et al. J. R. Soc. Interface, 2008, 5, S151-S159.*
Kalaganov, "Rapid Method for Determination Hydrogen Sulfide-producing Bacteria in Water-miscible cutting Fluids"; Neftepererabotka I Neftekhimiya (Moscow, Russian Federaiont); 1988, vol. 10, pp. 18-19—Translation.
Postgate, "Versatile Medium for the Enumeration of Sulfate-Reducing Bacteria", Appl. Microbiol., 1963, vol. 11, pp. 265-267.
Vester, "Improved Most-Probable-Number Method to Detect Sulfate-Reducing Bacteria with Natural Media and a Radiotracer", Applied and Environmental Microbiology, 1998, vol. 64, No. 5, pp. 1700-1707.
International Search Report for PCT International Application No. PCT/US2016/053863, dated Dec. 20, 2016, 5pgs.

* cited by examiner

*Primary Examiner* — Bin Shen

(74) *Attorney, Agent, or Firm* — Qiang Han

(57) ABSTRACT

In one aspect, the present disclosure provides a device. The device includes a body comprising a waterproof base, a waterproof coversheet attached to the base, and a channel disposed between the base and the coversheet. The channel has a perimeter and an opening that provides liquid access to the channel. A portion of the perimeter is defined by a waterproof seal. A dry first oxygen-scavenging reagent and an indicator reagent for detecting sulfate reduction by a sulfate-reducing bacterium are disposed in the device between the base and the coversheet. The waterproof base comprises a plurality of open microcompartment structures facing the coversheet.

20 Claims, 3 Drawing Sheets

SELF-CONTAINED ANAEROBIC CULTURE DEVICE WITH MICROCOMPARTMENTS

CROSS REFERENCE TO RELATED APPLICATIONS

This application claims priority to U.S. Provisional Patent Application No. 62/233,567, filed Sep. 28, 2015, the disclosure of which is incorporated by reference in its entirety herein.

BACKGROUND

Many industries need to detect and quantify biological material in a sample, for instance, the determination of microbial concentration in food and water is an essential part of food and water quality testing. Similar demands arise from a multitude of industries including food, biotechnological, pharmaceutical, water treating industry, and also in medical microbiological diagnostics, environmental and scientific research. Samples are commonly scrutinized to, for instance, monitor microbial population in a production environment, in-process controls, post storage and also final product testing.

Classical methods for the examination of samples particularly liquid samples typically demands incubation time or reaction time for analysis. Analysis may involve several different kinds of chemical, biochemical, physical or optical techniques and require many hours or even days for incubation and subsequent analysis. Reducing the time for quantitative and qualitative analysis of samples is very essential for making rapid decisions in quality and process control operations.

With regard to testing of aqueous biological samples, it is advantageous to partition the sample into aliquots so that the desired reaction or growth occurs and can be detected much more rapidly than the same reaction or growth in the original larger volume. Biological samples such as microbiological samples and molecular biology samples would often require such partitioning, in order to be analyzed precisely qualitatively and/or quantitatively.

Many bacteria are sensitive to oxygen and will not grow in its presence. It can be useful in various environments to determine the viability of such anaerobic microorganisms. For example, it can be important to determine if anaerobic microorganisms are present in food processing and/or packaging facilities. It can also be important to determine the presence of anaerobic microorganisms in medical environments, for example, to determine the presence of pathogens in diagnostic assays. As another example, water treatment facilities test water samples to determine the presence or absence of such microbes.

In addition, it can be difficult to provide an environment suitable for culturing anaerobic microorganisms using Petri dishes. Because anaerobic microorganisms do not thrive in the presence of oxygen, cumbersome physical and chemical techniques can be required to grow such organisms. Typically, such devices must be modified, i.e., shaped or configured, to provide a physical barrier to the transmission of oxygen.

Other techniques have been developed that use chemical agents incorporated into an anaerobic culturing device to remove oxygen. Generally, such devices include a reducing agent or sterile membrane fragments of bacteria incorporated into a gel or nutrient media. In addition, U.S. Pat. No. 3,338,794 describes an anaerobic bacteria culturing device formed of oxygen impermeable film layers and a nutrient media between the films, which includes a reducing compound.

These and other devices, however, can also be cost prohibitive and may not be readily disposable. These devices can also be cumbersome to assemble and/or use. Although attempts have been made to produce a simple device for culturing anaerobic microorganisms in an aerobic environment, there remains a need for improved anaerobic culture devices.

SUMMARY

In general, the present disclosure relates to detection and, optionally, enumeration of microorganisms in a sample. In particular, the present disclosure relates to growth and detection of obligately-anaerobic microorganisms. The growth and detection can be conducted using a self-contained modified environment-generating culture device. The modified environment-generating device is activated with an aqueous liquid to produce an aqueous growth medium that has a reduced concentration of dissolved oxygen and, optionally, an increased concentration of dissolved carbon dioxide.

The inventive culture device and methods disclosed herein provide for growth, detection, and differentiation of obligately-anaerobic microorganisms even while incubating the culture device in oxygen-containing (e.g., normal atmospheric oxygen-containing) environments. Advantageously, this eliminates the need for specialized incubation equipment and reagents (e.g., anaerobe jars, single-use anaerobe sachets, palladium catalysts, anaerobic glove boxes) that are typically required to culture obligately-anaerobic microorganisms. Additionally, the inventive methods provide for differentiation of bacteria by permitting detecting the production of carbon dioxide gas from individual colonies, thus eliminating the additional incubation time needed for isolation of pure cultures and the use of fermentation tubes to detect gas production. Obligately-anaerobic microorganisms share the common feature that they require reduced-oxygen environments in which to grow and reproduce.

In one aspect, the present disclosure provides a culture device for detecting and enumerating microorganisms in a sample. The device can comprise a body and a dry first oxygen-scavenging reagent. The body can comprise a waterproof base, a waterproof coversheet attached to the base, and a channel disposed between the base and the coversheet. The waterproof base can comprise a plurality of open microcompartment structures facing the coversheet. The channel can have a perimeter and a sealable opening that provides liquid access to the channel. A portion of the perimeter is defined by a waterproof seal. The portion can include >50% of the perimeter. The first oxygen-scavenging reagent can be disposed in the device between the base and the coversheet. In any embodiment, the device further can comprise an indicator reagent for detecting sulfate reduction by a sulfate-reducing bacterium, wherein the indicator reagent is disposed in the device between the base and the coversheet. In any embodiment, the device further can comprise a dry culture medium component disposed in the device between the base and the coversheet, wherein the culture medium component is selected to facilitate growth of a sulfate-reducing bacterium.

In any of the above embodiments, the waterproof base can have a first adhesive layer disposed on a major surface facing the coversheet. A first dry component can be adhered to the first adhesive layer. The first dry component is selected from the group consisting of the first oxygen-scavenging reagent, the second oxygen-scavenging reagent, the reducing agent, the indicator reagent, the culture medium component, and a combination of any two or more of the foregoing first dry components.

In any of the above embodiments, the waterproof coversheet can have a second adhesive layer disposed on a major surface facing the base. A second dry component can be adhered to the second adhesive layer. The second dry component is selected from the group consisting of the first oxygen-scavenging reagent, the second oxygen-scavenging reagent, the reducing agent, the indicator reagent, the culture medium component, and a combination of any two or more of the foregoing second dry components.

In another aspect, the present disclosure provides a method of detecting and enumerating microorganisms in a sample. The method can comprise depositing a sample into a channel of a device. The device can comprise a body and a dry first oxygen-scavenging reagent. The body can comprise a waterproof base, a waterproof coversheet attached to the base, and a channel disposed between the base and the coversheet. The waterproof base comprises a plurality of open microcompartment structures disposed in the device facing the coversheet. The channel can have a perimeter and a sealable opening that provides liquid access to the channel. A portion of the perimeter is defined by a waterproof seal. The first oxygen-scavenging reagent can be disposed in the device between the base and the coversheet. In any embodiment, the device further can comprise an indicator reagent for detecting sulfate reduction by a sulfate-reducing bacterium, wherein the indicator reagent is disposed in the device between the base and the coversheet. In any embodiment, the device further can comprise a dry culture medium component disposed in the device between the base and the coversheet, wherein the culture medium component is selected to facilitate growth of a sulfate-reducing bacterium. The method further can comprise isolating portions of the sample in the plurality of the microcompartments of the device, incubating the device at a temperature that facilitates growth of a sulfate-reducing microorganism for a period of time sufficient to detect an indication of a presence of the sulfate-reducing microorganism in at least one of the microcompartments, and detecting the indication in at least one of the microcompartments or detecting an absence of the indication in all of the microcompartments of the culture device.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

As used herein, "a," "an," "the," "at least one," and "one or more" are used interchangeably. Thus, for example, a nutrient can be interpreted to mean "one or more" nutrients.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The term "microorganism" or "microbe" as used herein refers to any microscopic organism, which may be a single cell or multicellular organism. The term is generally used to refer to any prokaryotic or eukaryotic microscopic organism capable of growing and reproducing in a suitable culture medium, including without limitation, one or more of bacteria. Microorganisms encompassed by the scope of the present invention include prokaryotes, namely the bacteria and archaea; and various forms of eukaryotes, comprising the protozoa, fungi, yeast (e.g., anaerobic yeast), algae etc. The term "target microorganism" refers any microorganism that an operator desires to detect.

The term "anaerobic microorganism" or "anaerobe" as used herein refers to microorganisms which are sensitive to oxygen and will not grow in the presence of oxygen. An anaerobic microorganism or anaerobe is any organism that does not require oxygen for growth. Anaerobic microorganisms include both obligate anaerobes and facultative anaerobes. "Obligate anaerobes" are those microorganisms which will die when exposed to atmospheric levels of oxygen. A "facultative anaerobe" is an organism that can carry out aerobic respiration if oxygen is present, but is capable of switching to fermentation or anaerobic respiration if oxygen is absent. Methods and systems of the present invention could be used for the enrichment and detection of both obligate anaerobes and facultative anaerobes.

The term "culture" or "growth" of microorganisms as used herein refers to the method of multiplying microbial organisms by letting them reproduce in predetermined culture media under conditions conducive for their growth. More particularly it is the method of providing a suitable culture medium and conditions to facilitate at least one cell division of a microorganism. Culture media are solid, semi-solid or liquid media containing all of the nutrients and necessary physical growth parameters necessary for microbial growth.

The term "enrichment" as used herein refers to the culture method of selectively enriching the growth of a specific microorganism by providing medium and conditions with specific and known attributes that favors the growth of that particular microorganism. The enrichment culture's environment will positively influence the growth of a selected microorganism and/or negatively influence the growth of other microorganisms.

"Oxygen scavenging reagent" and "oxygen scavenger" will be used broadly herein to refer to a compound that can consume, deplete or react with oxygen from a given environment. Preferably, the oxygen scavenging reagent does not slow or inhibit growth of anaerobic microorganisms.

The term "reducing agent" refers to a substance that is capable of lowering the $E_h$ potential of the semisolid culture medium formed by hydration of the dry components in the channel of a device of the present disclosure.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Additional details of these and other embodiments are set forth in the accompanying drawings and the description below. Other features, objects and advantages will become apparent from the description and drawings, and from the claims.

DETAILED DESCRIPTION

Figure 1:
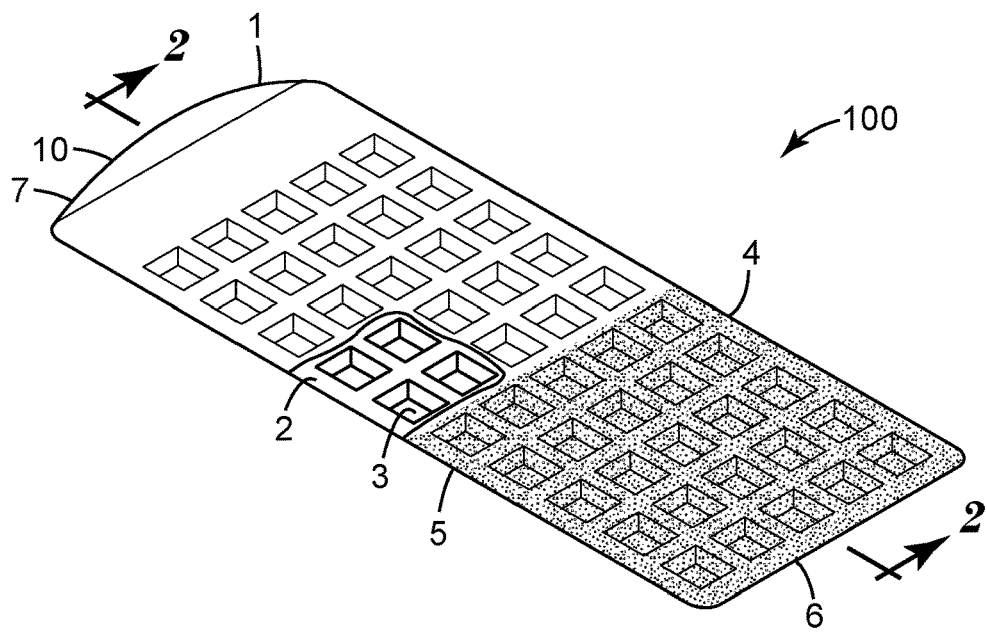
FIG. 1 is a perspective view, partially in section, of one embodiment of a culture device according to the present disclosure.

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "connected" and "coupled" and variations thereof are used broadly and encompass both direct and indirect connections and couplings. Further, "connected" and "coupled" are not restricted to physical or mechanical connections or couplings. It is to be understood that other embodiments may be utilized and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure generally relates to detection and, optionally, enumeration of anaerobic microorganisms in a sample. Certain microorganisms are considered facultatively-anaerobic microorganisms. Accordingly, they can grow in the presence or absence of oxygen. These microorganisms, as well as obligately-anaerobic microorganisms, can be selectively-enriched over strictly-aerobic microorganisms by cultivating them in a reduced-oxygen or anaerobic environment. A device of the present disclosure advantageously can be used to selectively enrich facultatively-anaerobic and obligately-anaerobic microorganisms present in a sample that also contains strictly-aerobic microorganisms.

It is now known that a dry, rehydratable self-contained reduced-oxygen environment-generating culture devices can be made. The culture device comprises an effective amount of a substantially-dry oxygen-scavenging reagent disposed in a channel of the culture device and being capable of rehydration in a predetermined volume of aqueous solution wherein, upon rehydration, the dry oxygen-scavenging reagent is capable of participating in an oxygen-consuming reaction. Further, it is now known the oxygen-consuming reaction can consume enough oxygen to facilitate growth of a microaerotolerant microorganism, a microaerophilic microorganism, or an obligately-anaerobic microorganism. Moreover, the culture device can be held in an aerobic environment during incubation wherein the culture device can maintain a reduced oxygen environment for up to about eight days in order to facilitate growth of the aforementioned microorganisms.

Test samples used in a method according to the present disclosure may include liquids as well as solid(s) dissolved or suspended in a liquid medium. Samples of interest may include process streams, water, soil, plants or other vegetation, air, surfaces (e.g., walls, floors, equipment, utensils in a manufacturing plant or home, for example), and the like.

Anaerobic bacteria are ubiquitous in nature. The anaerobic bacteria can be obligately-anaerobic or, alternatively can be facultatively-anaerobic. Nonlimiting examples of obligately-anaerobic bacteria include sulfate-reducing bacteria (SRB; such as *Desulfovibrio* spp. and *Desulfotomaculum* spp., for example).

Figure 2:
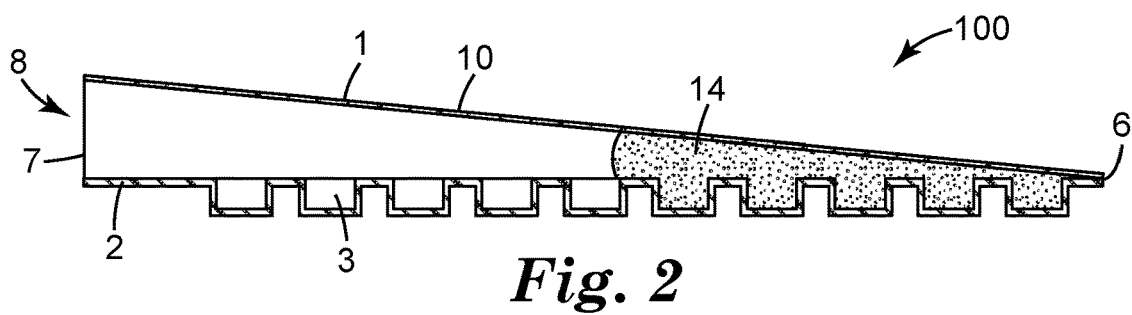
FIG. 2 is a cross-sectional view, along line 2-2, of the culture device of FIG. 1, showing a plurality of microcompartments and a dry composition disposed in the culture device.

In one aspect, the present disclosure provides a culture device for culturing and detecting a microorganism that grows in reduced-oxygen environments. One embodiment of a device according to the present disclosure is illustrated in FIGS. 1-2. Referring first to FIG. 1, device 100 is shaped generally like a combination bag/ice-cube tray. Device 100 is formed of two generally rectangular sheets, coversheet 1 and base 2. Coversheet 1 is substantially flat (e.g., sheetlike) and is made of a waterproof material such as, for example, a plastic polymer or a polymer-coated paper. Base 2 can be made of a waterproof, light-transmissible material such as, for example, polyvinylchloride.

Referring to FIGS. 1-2, base 2 is formed to have a plurality of microcompartments 3 which protrude on one side of the base in a direction away from the coversheet 1. In the illustrated embodiment, there are fifty microcompartments 3 of equal size which each hold approximately 2 ml of liquid. Coversheet 1 and base 2 are sealed together along the perimeter of the device 100; e.g., along the length of the two long edges 4 and 5, and along one narrow edge 6. At least a portion of the fourth edge 7 of the perimeter of the device 100 is left unsealed to create an opening through which the sample can be added to the article. Other than the three sealed edges, coversheet 1 and base 2 are not sealed or attached, leaving a channel 8 between coversheet 1 and base 2 into which a liquid sample is deposited and distributed throughout the device 100 and among all the microcompartments. Disposed in the channel is a dry composition 14.

Base 2 is preferably a relatively stiff waterproof film made of a material (e.g., polyester, polypropylene, or polystyrene) that will not absorb or otherwise be adversely affected by water. Base 2 preferably is made using a material that is substantially nontransmissible to gaseous oxygen. Nonlimiting examples of suitable materials for base 2 include polyester films at least about 15 μm to at least about 180 μm thick, polypropylene films at least about 100 μm to at least about 200 μm thick and polystyrene films at least about 300 μm to about 380 μm thick. Other suitable bases include ethylene vinyl alcohol copolymer films, polyvinyl alcohol films, and polyvinylidene chloride films. Base 2 can be opaque, translucent, or, if observing an indication of microbial growth through the base 2 is desired, the base may be transparent.

The coversheet 1 is attached (e.g., adhesively attached) to the base 2 to define the channel 8 and; optionally, if the coversheet is optically transmissive; to view the channel during shipping, storage, incubation, and/or while detecting an indication of microbial growth. Coversheet 1 comprises a substrate 10 that is preferably a relatively stiff waterproof film made of a material (e.g., polyester, polypropylene, or polystyrene) that will not absorb or otherwise be adversely affected by water. Coversheets 1 are preferably transparent in order to facilitate viewing the microcompartments without opening the culture device 100, and are substantially impermeable to microorganisms and water vapor.

Figure 3:
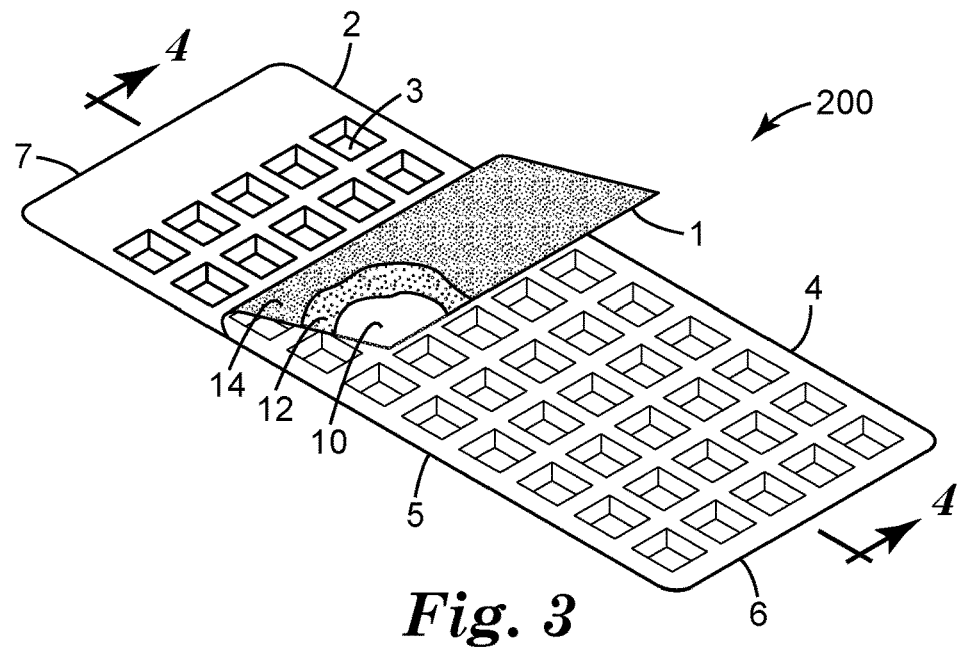
FIG. 3 is a perspective view, partially in section, of an alternative embodiment of a culture device according to the present disclosure.

Generally, coversheets can be made of materials such as those used to make base 2. Coversheet 1 preferably is made using a material that is substantially nontransmissible to gaseous oxygen. Nonlimiting examples of suitable materials for base 2 include polyester films at least about 15 µm to at least about 180 µm thick, polypropylene films at least about 100 µm to at least about 200 µm thick and polystyrene films at least about 300 µm to about 380 µm thick. Other suitable bases include ethylene vinyl alcohol copolymer films, polyvinyl alcohol films, and polyvinylidene chloride films. As shown in FIG. 3, the coversheet 1 is bonded to the base 2 (e.g., via a pressure-sensitive adhesive or hot-melt adhesive) along a portion (e.g., three sides) of the perimeter of the channel.

A person having ordinary skill in the art will recognize the transmissibility of oxygen gas through a given type of polymer film can be reduced by increasing the thickness of the polymer film. In any embodiment, the base and coversheet of the present disclosure are polymeric films having a suitable thickness to be substantially nontransmissible to gaseous oxygen.

The channel 8 can be at any accessible location in the culture device 100 between the base 2 and the coversheet 1. Preferably, the opening of the channel 8 is large enough to accommodate an article (e.g., a pipet) that is used to transfer a liquid sample into the device.

The dry composition 14 comprises an effective amount of one or more dry oxygen-scavenging reagent. The one or more dry oxygen-scavenging reagent is disposed in the device (e.g., in the channel and/or in one or more of the microcompartments). "Dry", as used herein, means the reagent is substantially water-free. The phrase "substantially water-free" refers to a reagent that has a water content no greater than about the water content of the material (e.g., provided as a powder or as a dehydrated aqueous coating) once it has been permitted to equilibrate with the ambient environment. In any embodiment, the dry composition 14 may be uniformly distributed in the culture device, as described hereinbelow.

A number of suitable dry oxygen-scavenging reagents are known including, for example, ascorbic acid (e.g., L-ascorbic acid and salts thereof), ferrous iron salts, metal salts of sulfite, bisulfate, and metabisulfite. A suitable dry oxygen-scavenging reagent according to the present disclosure consumes enough oxygen to create a low-oxygen or anaerobic local environment in the culture device and produces quantities and types of reaction products that can be in fluidic communication with the microorganisms to be cultured in the device without substantially inhibiting growth of those microorganisms. In any embodiment, the dry oxygen-scavenging reagent is disposed in the device in a quantity sufficient to attain a concentration of less than or equal to 10 nM (e.g., less than 10 nM, less than 5 nM, less than 2 nM, less than 1 nM, or 0 nM) when dissolved in a predefined volume of aqueous sample material. Accordingly, the quantity of dry oxygen-scavenging reagent in the culture device is in molar excess with respect to the expected quantity of oxygen in the aqueous liquid used to inoculate the device.

In any embodiment, the quantity (e.g., in moles) of dry oxygen-scavenging reagent can be about 2-times the expected quantity of oxygen in the aqueous liquid used to inoculate the device. In any embodiment, the quantity of dry oxygen-scavenging reagent can be about 3-times the expected quantity of oxygen in the aqueous liquid used to inoculate the device. In any embodiment, the quantity of dry oxygen-scavenging reagent can be about 5-times the expected quantity of oxygen in the aqueous liquid used to inoculate the device. In any embodiment, the quantity of dry oxygen-scavenging reagent can be about 10-times the expected quantity of oxygen in the aqueous liquid used to inoculate the device. In any embodiment, the quantity of dry oxygen-scavenging reagent can be about 20-times the expected quantity of oxygen in the aqueous liquid used to inoculate the device. In any embodiment, the quantity of dry oxygen-scavenging reagent can be about 50-times the expected quantity of oxygen in the aqueous liquid used to inoculate the device. In any embodiment, the quantity of dry oxygen-scavenging reagent can be about 200-times the expected quantity of oxygen in the aqueous liquid used to inoculate the device.

Figure 4:
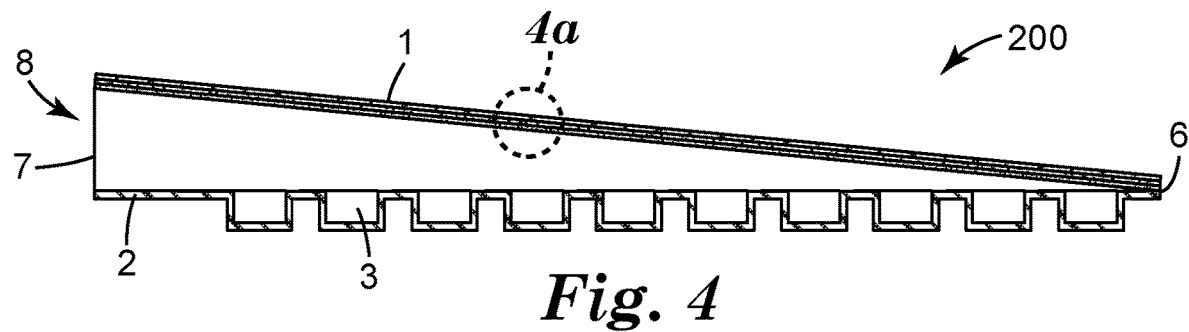
FIG. 4 is a cross-sectional view, along line 4-4, of the culture device of FIG. 3.
Figure 4A:
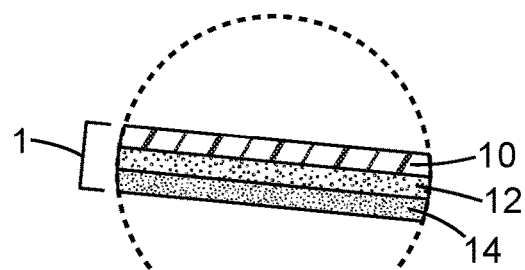
FIG. 4a is a cross-sectional detail view of the layers coated onto the coversheet of FIG. 4.

Referring back to the drawings, FIGS. 3-4a show various views of an alternative embodiment of a culture device 200 according to the present disclosure. The culture device 200 comprises a coversheet 1 adhered to a base 2 along a portion of its perimeter (e.g., along edges 4, 5, and 6, as described above) and a channel 8 disposed between the coversheet and the base. The base 2 has a plurality of microcompartments 3 formed therein, as described above.

FIG. 3 shows the coversheet 1 partially lifted back from the base 2 in order to show the layers coated on to the inner surface of the coversheet. However, in use, the coversheet normally 1 is sealed along the entire length of edges 4 and 5 as depicted in FIG. 4. In these embodiments, the coversheet 1 comprises a substrate 10 (as described above) with a dry composition adhered thereto. In these embodiments, the dry composition 14 is present in the device 200 adhered to at least a portion or all of the inner surface (i.e., the surface facing the base 2) of the coversheet 1. The dry composition 14 comprises the one or more dry oxygen-scavenging reagent, as described herein. Other suitable components of the dry composition 14 are discussed hereinbelow. Optionally, an adhesive layer 12 is adhered to the coversheet 1 and the dry composition 14 is adhered to the first adhesive layer. In any embodiment, the dry composition 14 can be uniformly distributed on the inner surface of the coversheet 1.

Figure 5:
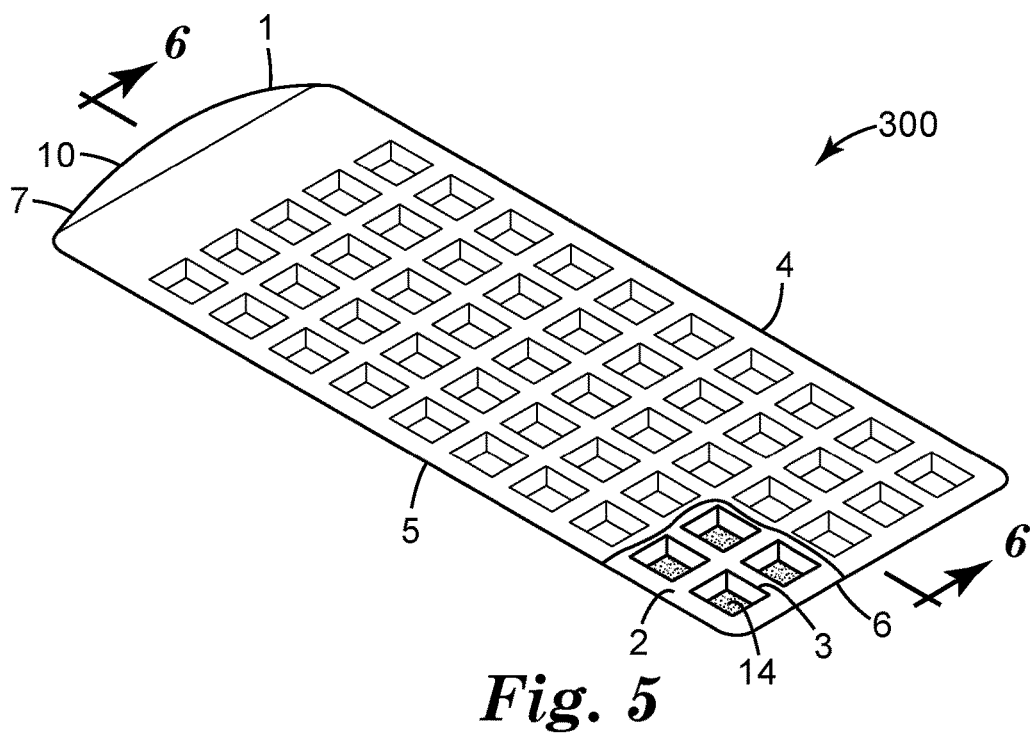
FIG. 5 is a perspective view, partially in section, of another alternative embodiment of a culture device according to the present disclosure.
Figure 6:
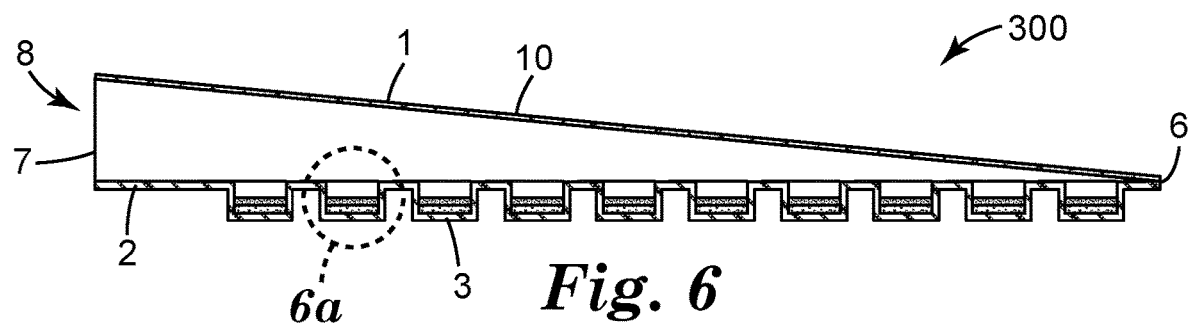
FIG. 6 is a cross-sectional view of the culture device of FIG. 5.
Figure 6A:
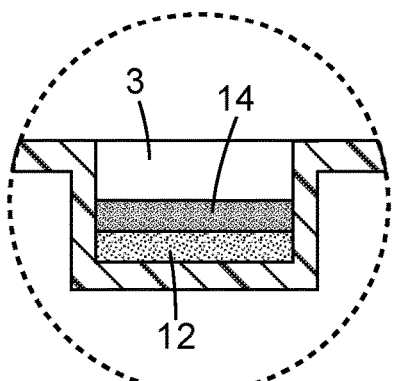
FIG. 6a is a cross-sectional detail view of the layers coated onto one of the microcompartments of FIG. 6.

FIGS. 5-6a show various views of another alternative embodiment of a culture device 300 according to the present disclosure. The culture device 300 comprises a coversheet 1 (as described herein) adhered to a base 2 along a portion of its perimeter (e.g., along edges 4, 5, and 6, as described above) and a channel 8 disposed between the coversheet and the base. The base 2 has a plurality of microcompartments 3 formed therein, as described above.

In these embodiments, dry composition 14 is present in the device 300 in a second coating adhered to at least a portion of the inner surface (i.e., the surface facing the coversheet 1) of each microcompartment 3 of the base 2. The dry composition 14 comprises the one or more dry oxygen-scavenging reagent, as described herein. Other suitable components of the dry composition 14 are discussed hereinbelow. Optionally, an adhesive layer 12 is adhered to the base 1 in the microcompartments 3 and the dry composition 14 is adhered to the first adhesive layer in each microcompartment.

In yet another embodiment (not shown), a device of the present disclosure comprises a coversheet adhered to a base along a portion of its perimeter, as described above, and a channel disposed between the coversheet and the base. The base has a plurality of microcompartments formed therein, as described above. In addition, the coversheet has any embodiment of a dry composition as described herein adhered to the inner surface of the coversheet and the base has any embodiment of a dry composition as described herein adhered to the inner surface of each microcompartment. The dry composition adhered to the coversheet can be the same dry composition adhered to the base or it can be a different embodiment of the dry composition disclosed herein.

Preferably, in any embodiment, the one or more dry oxygen-scavenging reagents are provided in the dry composition 14 in the form of a dry powder. More preferably, in any embodiment, the one or more dry oxygen-scavenging reagent is provided as a dry powder that is milled and classified to form a population of particles with a size distribution consisting essentially of particles having a diameter of 100 microns or less.

Advantageously, an oxygen-scavenging reagent provided in particles having a diameter of 100 microns or less can be adhered; optionally, with other dry reagents; to the base 2 or the coversheet 1 (e.g., adhered to an adhesive layer coated onto the base or coversheet) in an amount effective to create and maintain (e.g., up to about 24 hours of incubation, up to about 48 hours of incubation, up to about 72 hours of incubation, up to 4 days of incubation, up to 5 days of incubation, up to 7 days of incubation, at least 24 hours of incubation, at least 48 hours of incubation, at least 72 hours of incubation, at least 4 days of incubation, at least 5 days of incubation, at least 7 days of incubation) an anaerobic environment in the microcompartments when the device is inoculated with a predefined volume of aqueous liquid and a plurality of the microcompartments are isolated as described herein.

In any embodiment, the dry composition 14 optionally comprises a dry culture medium component that facilitates growth of a sulfate-reducing microorganism. Preferably, the culture medium component is cold-water-reconstitutable and does not substantially interfere with the dry oxygen-scavenging reagent. The particular culture medium component suitable for use in the culture device will depend on the microorganism to be grown in the device, and will be easily selected by those skilled in the art. Generally, such components (e.g., nutrients) are cold-water soluble. Suitable nutrients for supporting bacterial growth are known in the art and include without limitation yeast extract, peptone, sugars, suitable salts, and the like. In any embodiment, the first and/or second dry coating further can comprise a selective agent (e.g., a nutrient, an antibiotic, and combinations thereof) that facilitates the growth of a particular anaerobic microorganism or group of microorganisms over another microorganism or group of microorganisms. Those skilled in the art will recognize that a variety of other formulations could be used and that these do not detract from the scope of this invention.

In any embodiment, the dry culture medium component is an organic carbon source. In any embodiment, the organic carbon source is nonfermentable.

Preferably, when the dry composition consists primarily of dry powder or dry powder agglomerate, the dry composition is disposed in a first coating adhered to an adhesive layer on at least a portion of the inner surface of the coversheet and/or the dry composition is disposed in a second coating adhered to an adhesive layer on at least a portion of the inner surface of the base. The dry composition can be deposited onto the coversheet, the base or onto the optional adhesive layer(s) using compounding processes, adhesive coating processes, and liquid-coating processes and/or dry-coating processes described, for example, in U.S. Pat. Nos. 4,565,783; 5,089,413; and 5,232,838; which are all incorporated herein by reference in their entirety.

Preferably, when the dry composition consists primarily of dry powder or dry powder agglomerate, the dry composition is disposed on a first adhesive layer that is disposed on at least a portion of the inner surface of the coversheet. The dry composition can be deposited onto the coversheet or onto the optional second adhesive layer using compounding processes, adhesive coating processes, and liquid-coating processes and/or dry-coating processes described, for example, in U.S. Pat. Nos. 4,565,783; 5,089,413; and 5,232,838; which are all incorporated herein by reference in their entirety.

The channel 8 is defined as a volume disposed between the inner surfaces of the base 2 and coversheet 1, the volume encompassing at least a portion of the first dry coating and/or the second dry coating. Thus, when an aqueous liquid (not shown) is distributed into the channel 8, the aqueous liquid is in fluidic contact with at least a portion of the first dry coating, if present, and/or second dry coating, if present.

Optionally, the dry composition 14 of the present disclosure further can comprise other dry, water-rehydratable dry components such as a component of a buffer, a reducing agent, an indicator reagent and/or an effective amount of a carbon dioxide-generating reagent.

At least one dry component (e.g., the one or more oxygen scavenging reagent) is hydrated with an aqueous liquid before, during, or after the introduction (e.g., inoculation) of sample material into the channel of the culture device, as described herein. Typically, the sample material and/or aqueous liquid is introduced into the channel of the culture device in ambient conditions (i.e., in an aerobic gaseous environment). Thus, after inoculation of the channel and/or microcompartments with a sample under aerobic conditions, the aqueous liquid in the channel and/or microcompartments of the culture device comprises a first dissolved-oxygen concentration. The one or more dry oxygen-scavenging reagent in the culture device functions to reduce the first dissolved-oxygen concentration in the aqueous liquid in the isolated microcompartments to a second dissolved-oxygen concentration that is substantially lower than the first dissolved-oxygen concentration. This reduction of the dissolved oxygen concentration in the isolated microcompartments of the inoculated culture device facilitates the growth of obligately-anaerobic microorganisms in the culture device.

In any embodiment, the effective amount of the one or more dry oxygen-scavenging reagent and quantity thereof is selected such that reducing the first dissolved oxygen concentration to the second dissolved oxygen concentration occurs within about 120 minutes after bringing the one or more dry oxygen-scavenging reagent into fluidic contact with the predefined volume of aqueous liquid in the culture device. In any embodiment, the effective amount of the one or more dry oxygen-scavenging reagent and quantity thereof is selected such that reducing the first dissolved oxygen concentration to the second dissolved oxygen concentration occurs within about 60 minutes after bringing the dry oxygen-scavenging reagent into fluidic contact with the predefined volume of aqueous liquid in the culture device. In any embodiment, the effective amount of the one or more dry oxygen-scavenging reagent and quantity thereof is selected such that reducing the first dissolved oxygen concentration to the second dissolved oxygen concentration occurs within about 30 minutes after bringing the dry oxygen-scavenging reagent into fluidic contact with the predefined volume of aqueous liquid in the culture device.

In any embodiment, reducing the first dissolved oxygen concentration to the second dissolved oxygen concentration occurs at a temperature between ambient temperature (e.g., about 23 degrees C.) and about 42 degrees C., inclusive. Thus, in any embodiment of a method according to the present disclosure, it is not required to incubate the culture device at an elevated temperature (i.e., above ambient temperature) in order to reduce the first dissolved oxygen concentration to the second dissolved oxygen concentration after bringing the dry oxygen-scavenging reagent into fluidic contact with the predefined volume of aqueous liquid in the culture device.

A person having ordinary skill in the art will recognize the amount of oxygen removed from the isolated microcompartments of a culture device of the present disclosure within a period of time suitable for culturing microorganisms is dependent inter alia upon the quantity of the one or more dry oxygen-scavenging reagent in the isolated microcompartments of the culture device. By adjusting the amount of dry oxygen-scavenging reagent in the device according to the present disclosure, the culture device can be configured for culturing sulfate-reducing microorganisms.

Adhesive used in the optional adhesive layer 12 disposed on the coversheet 1 can be the same as or different from the adhesive used in the optional adhesive layer 12 disposed on the base 2. Coatings on coversheet 1 can cover the entire surface facing the base, but preferably cover at least a part of the inner surface that defines at least a portion of the channel 8 of the culture device 200.

In any embodiment, a selective agent may be disposed in the device in the dry composition or, optionally, dissolved in an adhesive layer within the channel and/or the microcompartments.

Optionally, a culture device of the present disclosure further comprises a means for indicating oxygen in a culture device. Preferably, the means is capable of indicating a quantity (e.g., either a predetermined threshold quantity or a relative quantity) of oxygen present in the device. Advantageously, the means can indicate whether or when the oxygen-scavenging reagent has suitably depleted the oxygen in the microcompartments of the culture device to a concentration that facilitates the growth of obligately-anaerobic microorganisms. Means for detecting oxygen in a culture device are known in the art and include, for example, redox dyes (e.g., methylene blue) and oxygen-quenched fluorescent dyes.

The means can be a luminescent compound that indicates the absence of oxygen inside of the device. Suitable oxygen indicators are disclosed in U.S. Pat. No. 6,689,438 (Kennedy et al.), which is incorporated herein by reference in its entirety. Luminescent compounds appropriate as indicators for a culture device of the present disclosure will display luminescence that is quenched by oxygen. More precisely, the indicators will luminesce upon exposure to their excitation frequency with an emission that is inversely proportional to the oxygen concentration. The indicator may be coated, laminated, or extruded onto another layer, or portion of another layer, within the device. Such a layer may be disposed in the microcompartments and optionally, is separated from the microcompartments by one or more other oxygen permeable layers. Suitable compounds for indicating oxygen include metallo derivatives of octaethylporphyrin, tetraphenylporphyrin, tetrabenzoporphyrin, the chlorins, or bacteriochlorins. Other suitable compounds include palladium coproporphyrin (PdCPP), platinum and palladium octaethylporphyrin (PtOEP, PdOEP), platinum and palladium tetraphenylporphyrin (PtTPP, PdTPP), camphorquinone (CQ), and xanthene type dyes such as erythrosin B (EB). Other suitable compounds include ruthenium, osmium and iridium complexes with ligands such as 2,2'-bipyridine, 1,10-phenanthroline, 4,7-diphenyl-1,10-phenanthroline and the like. Suitable examples of these include, tris(4,7,-diphenyl-1,10-phenanthroline)ruthenium(II) perchlorate, tris(2,2'-bipyridine)ruthenium(II) perchlorate, tris(1,10-phenanthroline)ruthenium(II) perchlorate, and the like.

Before inoculation, the dry composition included in a culture device of the present disclosure optionally includes an effective amount of a dry, carbon dioxide-generating reagent disposed in the channel and/or in one or more of the microcompartments. Without being bound by theory, the carbon dioxide-generating reagent, when activated by contact with an aqueous liquid, establishes an equilibrium of the following dissolved species: one or more salts of carbonic acid, carbonic acid, and carbon dioxide. Advantageously, the effective amount of carbon dioxide-generating reagent is sufficient to elevate the dissolved carbon dioxide to a concentration that facilitates growth of a variety of microorganisms.

Preferably, in any embodiment, the carbon dioxide-generating reagent is provided in the form of a dry powder. More preferably, in any embodiment, the carbon dioxide-generating reagent is provided as a dry powder that is milled and classified to form a population of particles with a size distribution consisting essentially of particles having a diameter of 100 microns or less. Advantageously, in particles having a diameter of 100 microns or less can be adhered to the base or the coversheet (e.g., adhered to an adhesive layer coated onto the base or coversheet) in an amount effective to create and maintain during an incubation period of several days a $CO_2$-enriched environment in the microcompartments after the device is inoculated with a predefined volume of aqueous liquid and closed. In any embodiment, before inoculation, the carbon dioxide-generating reagent can be adhered to an adhesive layer adhered to the base and/or the coversheet.

Before inoculation, the dry composition included in a culture device of the present disclosure optionally includes a dry buffer reagent disposed in one or more microcompartments and/or in the channel. When hydrated with deionized water, the buffer reagent brings the water to a predefined pH that is suitable for culturing, and optionally selectively-enriching, certain groups of microorganisms. For example, in any embodiment, the predefined pH may be about 5.2 to about 7.8. In any embodiment, the predefined pH may be less than or equal to 6.35 (e.g., about 4.5 to about 6.35). This slightly acidic pH provides several advantages: i) the acidic environment selectively favors growth of acid-tolerant microorganisms over other microorganisms that may be present in a sample and ii) the acidic environment can shift the equilibrium of the carbon generating reagent, if present, toward a higher proportion of dissolved $CO_2$, if desired. Both of these advantages can facilitate growth of anaerobic lactic acid bacteria, for example, in the culture device.

Buffer reagents used in a device of the present disclosure include any microbiologically-compatible buffer having a $pK_a$ of about 8.0 or less. The acidic and basic parts of the buffer reagent are present in the culture device in a ratio such that, when a predefined volume of deionized water is contacted with the buffer reagent, the pH of the in the microcompartments is suitable for growth and detection of a particular microorganism or group of microorganisms. Suitable buffer reagents include, for example, a metal phosphate salt, a metal acetate salt, 2-(N-morpholino)ethanesulfonic acid and sodium 2-(N-morpholino)ethanesulfonic acid, and succinic acid and sodium succinate. A person having ordinary skill in the art will recognize the ratio of acid an base buffer reagents can be adjusted in order to achieve the desired pH of the aqueous mixture formed when an predetermined volume of aqueous liquid (e.g., comprising the sample) is deposited in the channel and the device is closed in order to isolate a portion of the sample in each of the microcompartments.

A culture device of the present disclosure optionally includes an indicator reagent. Suitable indicator reagents (e.g., triphenyltetrazolium chloride (TTC)) may detect substantially all microorganisms present in the culture device. Optionally, the indicator reagent may be a differential indicator; i.e., the indicator reagent distinguishes certain microorganisms from other microorganisms. Suitable indicator reagents include, for example, a pH indicator, a redox indicator, a chromogenic enzyme substrate, and a fluorogenic enzyme substrate for detecting the presence of a microorganism. The indicator should not substantially interfere with the oxygen-scavenging reagent. In any embodiment, the indicator reagent may be disposed in the device in the dry composition or, optionally, it can be dissolved in an adhesive layer within the channel and/or the microcompartments.

In any embodiment, the dry composition included in culture device of the present disclosure optionally includes a reducing agent instead of, or in addition to, the dry oxygen-scavenging reagent. Suitable reducing reagents are useful to lower the oxidation-reduction potential of the growth medium and, thereby, facilitate growth of anaerobic microorganisms. Suitable reducing agents include, for example, sodium thioglycollate, L-cysteine, dithiothreitol, dithioerythritol, and combinations thereof. The reducing agent can be distributed (e.g., as a dry coating) on the coversheet and/or distributed in each microcompartment of the plurality of microcompartments.

In any embodiment, the plurality of microcompartments can be dimensioned so that the device can be inoculated with a 10 milliliter aqueous sample volume, for example. Water comprises about 0.54 μmoles of dissolved oxygen per milliliter. Thus, in this exemplary embodiment, the first dry coating and/or second dry coating preferably comprises at least enough oxygen-scavenging reagent to consume 5.4 μmoles of oxygen in a period of 120 minutes or less at about 22 degrees C. to about 42 degrees C. More preferably, the first dry coating and/or second dry coating preferably comprises at least enough dry oxygen-scavenging reagent to consume more than 5.4 μmoles of oxygen in a period of 120 minutes or less at about 22 degrees C. to about 42 degrees C. In any embodiment, the plurality of microcompartments can be dimensioned to receive with a liquid sample volume of about 1 milliliter to about 500 milliliters of aqueous liquid volume. A person having ordinary skill in the art will recognize the amount of dry oxygen-scavenging reagent should be adjusted in order to consume an amount of oxygen corresponding to the volume of aqueous sample to be tested.

In any embodiment, the dry composition can include any number of other components, such as dyes (e.g., a pH indicator), reagents (e.g., selective reagents or indicator reagents such as chromogenic or fluorogenic enzyme substrates), or a combination of any two or more of the foregoing components. For example, for some uses it is desirable to incorporate an indicator (e.g., a pH indicator, a chromogenic enzyme substrate, a redox dye) of microbial growth (e.g., growth of sulfate-reducing bacteria) in the dry composition or in an adhesive to which the first and/or second dry coating is adhered. Suitable dyes include those that are metabolized by or otherwise react with the growing microorganisms, and in so doing cause the colonies to be colored or fluorescent for easier visualization. Such dyes include triphenyl tetrazolium chloride, for example. Other suitable dyes include those sensitive to pH changes during the growth of microorganisms, such as neutral red.

In any embodiment, the dry composition included in a culture device of the present disclosure can optionally include reagents necessary for carrying out certain microbiological tests. For microorganism identification, differential reagents that undergo a color change in the presence of a particular type of microorganism can be included.

A culture device of the present can be prepared using a variety of techniques. Generally, a device can be made by hand or with common laboratory equipment as described herein and in U.S. Pat. No. 5,518,892; and in U.S. Patent Application No. 62/154,299, for example, which are both incorporated herein by reference in their entirety.

A nonlimiting example of a suitable pressure-sensitive adhesive that can be used in the first adhesive layer and/or second adhesive layer is a copolymer of 2-methylbutylacrylate/acrylic acid in a mole ratio of 90/10. Other preferred pressure sensitive adhesives that can be used include isooctylacrylate/acrylic acid in a mole ratio of 95/5 or 94/6 and silicone rubber. When incorporating an indicator reagent as described above in order to facilitate visualization of colonies, it is generally preferred to incorporate the indicator reagent in the adhesive or broth coating mixture, rather than in the powder.

The first adhesive layer or second adhesive layer is coated (e.g., using a knife coater or spray coater) onto the top surface of base or coversheet to form an adhesive layer at a thickness that is preferably less than the average diameter of the particles of dry powder or agglomerated powder to be adhered to the adhesive. Generally, enough adhesive is coated in order to adhere the particles to the substrate (e.g., the first or coversheet described herein) but not so much that the particles become completely embedded in the adhesive. Generally, an adhesive layer about 5 μm to about 12 μm thick is suitable.

A person having ordinary skill in the art will recognize suitable nutrients for use in the dry composition of a device of the present disclosure to grow and detect sulfate-reducing microorganisms. Non-limiting examples of suitable nutrients include a carbon source (e.g., a carbohydrate such as citrate or lactate), yeast extract, a source of sulfate (e.g., magnesium sulfate, calcium sulfate, ferric ammonium sulfate), and inorganic salts. Preferably, the carbohydrate is present in the device in an amount that is high enough to facilitate growth (biomass production) of the microorganisms. Nutrient media for culturing sulfate-reducing bacteria include, for example, Baar's medium and Postgate's B medium.

In another aspect, the present disclosure provides a first method of detecting sulfate-reducing microorganisms. The first method comprises depositing a sample into the channel of the device of any one of the embodiments described hereinabove. The first method further comprises isolating portions of the sample in a plurality of the microcompartments of the device, incubating the device at a temperature that facilitates growth of a sulfate-reducing microorganism for a period of time sufficient to detect an indication of a presence of the sulfate-reducing microorganism in at least one of the microcompartments, and detecting the indication in at least one of the microcompartments or detecting an absence of the indication in all of the microcompartments of the culture device. Advantageously, the culture device can be inoculated and/or incubated in an aerobic environment (i.e., in air).

Portions of the sample can be isolated in a plurality of microcompartments in the device while the sample is deposited into the channel of the device and/or after the sample is deposited into the sample of the device. Non-limiting examples of processes used to isolate portions of the sample in a plurality of the microcompartments are described in PCT Patent Publication No. WO 95/23026, which is incorporated herein by reference in its entirety. Preferably, the portions distributed into each microcompartment comprise approximately equal volumes. The portions can be isolated by forming a seal (e.g., by heat-sealing or by using a pressure-sensitive adhesive) around each portion.

In any embodiment of the method, placing the sample into the channel comprises placing one or more additive into the channel. The one or more additive can be placed into the channel with the sample or separately. The one or more additive may perform a variety of functions in the method. For example, in any embodiment, the one or more additive may comprise a nutrient or a nutrient medium to facilitate growth of sulfate-reducing microorganisms in the device. Such nutrients and nutrient media are well known in the art and may be selected based upon the particular microorganism to be cultured. The nutrient and nutrient medium should not substantially interfere with the oxygen-scavenging reagent. This can be tested readily by using an oxygen sensor as described in Examples 2-3 of PCT Patent Publication No. 2015/061213, which is incorporated herein by reference in its entirety.

After depositing the sample into the channel, the device is sealed (e.g., using a heat-sealing device such as a Quanti-Tray® sealer, for example). Sealing the device not only seals the opening, but it also seals the liquid in the individual microcompartments, thus dividing the sample into a plurality of aliquots. In any embodiment, the aliquots can all have an approximately-equal predetermined volume. In any embodiment, the aliquots can be partitioned such that there are more than one set of predetermined volumes. By distributing the sample into a plurality of aliquots having predetermined volumes, the device can be used to estimate the number of target microorganisms in the sample using a Most Probable Number calculation.

After isolating the portions of the sample, the device is incubated at a temperature that facilitates growth of a sulfate-reducing microorganism for a period of time sufficient to detect an indication of a presence of the sulfate-reducing microorganism in at least one of the microcompartments. The incubation conditions (e.g., the incubation temperature) can affect the rate of growth of the microorganisms, as is well known by a person having ordinary skill in the art. For example, incubation at lower temperatures (e.g., below about 25° C.) can allow for the detection of psychrotrophic microorganisms. Incubation at higher temperatures (e.g., about 30° C., about 32° C., about 35° C., about 37° C.) may facilitate faster growth of certain mesophilic microorganisms.

In some embodiments, after inoculation, the culture device can be incubated for at least about 16 hours, at least about 18 hours, at least about 24 hours, or at least about 48 hours. In some embodiments, the culture device can be incubated not more than about 24 hours, not more than about 48 hours, or not more than about 72 hours. In certain preferred embodiments, the culture device is incubated about 24 hours to about 48 hours. In any embodiment, the culture device can be incubated, and maintain a reduced-oxygen environment therein, for about 72 hours, for about 96 hours, for about 120 hours, for about 7 days, or for about 8 days before detecting or counting microcompartments that containing sulfate-reducing microorganisms. In any embodiment, incubating the culture device for a period of time sufficient to permit formation of a microbial colony comprises incubating the culture device for the period of time in an aerobic atmosphere (i.e., the culture device is not placed into a reduced-oxygen container or glovebox for incubation).

In any embodiment, detecting an indication of a presence of the sulfate-reducing microorganism in at least one of the microcompartments comprises detecting a change of an indicator reagent form a first state (e.g., a colorless state and/or a nonfluorescent state) to a second state (e.g., a colored state or a fluorescent state). In any embodiment, detecting an indication of a presence of the sulfate-reducing microorganism in at least one of the microcompartments comprises detecting a change of a substantially colorless indicator compound comprising an oxidized sulfur atom (e.g., ferrous sulfate) to a colored compound comprising a reduced sulfur atom (e.g., iron (II) sulfide).

In any embodiment, the first method further comprises depositing an aqueous liquid into the channel. In these embodiments, the aqueous liquid can be used to dilute a sample comprising aqueous liquid or non-aqueous material (e.g., organic liquid, solids such as particulate solids) and optionally can be used to provide a more-homogeneous liquid suspension of the sample material. Diluting the sample material can ensure that the sample is suspended in enough volume to fill all of the microcompartments with approximately-equal volumes of liquid. Depositing the aqueous liquid into the channel can occur before, after, or simultaneous with depositing the sample into the channel. In any embodiment, the sample is disposed in the aqueous liquid prior to depositing the aqueous liquid into the channel.

In any embodiment, depositing the aqueous liquid into the channel comprises depositing a predetermined volume of the aqueous liquid. In any embodiment, the predetermined volume can be about 1.0 mL to about 200 mL. For example, the predetermined volume can be about 1 mL, about 5 mL, about 10 mL, about 20 mL, about 25 mL, about 50 mL, about 100 mL, about 125 mL, about 150 mL, or about 200 mL. In any embodiment of the method, placing the predetermined volume into the channel comprises simultaneously placing the sample into the channel. For example, the sample may be a liquid (e.g., a water or beverage sample to be tested for microbial contamination) or the sample may be a solid or semisolid sample suspended in a liquid carrier or diluent.

In any embodiment, the method further comprises sealing the opening of the device. Sealing the opening can comprise heat-sealing the opening, for example, as described in PCT Patent Publication No. WO 95/23026.

In any embodiment, incubating the device comprises incubating the device for a period of 7 days or less. In any embodiment, incubating the device comprises incubating the device for a period of 96 hours or less. In any embodiment, incubating the device comprises incubating the device for a period of 72 hours or less. In any embodiment, incubating the device comprises incubating the device for a period of 48 hours or less. In any embodiment, incubating the device comprises incubating the device for a period of 24 hours or less. In any embodiment, incubating the device comprises incubating the device in an oxygen-containing (e.g., ambient oxygen) atmosphere.

In any embodiment, the first concentration of dissolved oxygen in the aqueous mixture in the channel and/or microcompartments may be a concentration that substantially inhibits growth of an obligately-anaerobic microorganism. In these embodiments, depositing the sample in the channel and/or the microcompartments causes contact between the aqueous mixture and the one or more oxygen-scavenging reagent, which initiates an oxygen-scavenging reaction, thereby reducing the first concentration of dissolved oxygen in the aqueous liquid in the isolated microcompartments to a second concentration that is lower than the first concentration (e.g., at least about 50% lower, at least about 60% lower, at least about 70% lower, at least about 80%, at least about 90%, at least about 95%, at least about 98%, at least about 99% lower, or greater than 99% lower than the first concentration).

In any embodiment, reducing the first concentration of dissolved oxygen to the second concentration of dissolved oxygen can comprise reducing the dissolved oxygen in the aqueous mixture in the isolated microcompartments to a second concentration that is low enough to support the growth of anaerobic microorganisms (e.g., sulfate-reducing bacteria).

In any embodiment, reducing the first concentration of dissolved oxygen to the second concentration of dissolved oxygen comprises reducing the dissolved oxygen to the second concentration in the aqueous mixture in the channel and/or the microcompartments in less than or equal to about 120 minutes after the mixture is formed. In any embodiment, reducing the first concentration of dissolved oxygen to the second concentration of dissolved oxygen comprises reducing the dissolved oxygen to the second concentration in the aqueous mixture in the channel and/or the microcompartments in less than or equal to about 90 minutes after the mixture is formed. In any embodiment, reducing the first concentration of dissolved oxygen to the second concentration of dissolved oxygen comprises reducing the dissolved oxygen to the second concentration in the aqueous mixture in the channel and/or the microcompartments in less than or equal to about 60 minutes after the mixture is formed. In any embodiment, reducing the first concentration of dissolved oxygen to the second concentration of dissolved oxygen comprises reducing the dissolved oxygen to the second concentration in the aqueous mixture in the channel and/or the microcompartments in less than or equal to about 45 minutes after the mixture is formed. In any embodiment, reducing the first concentration of dissolved oxygen to the second concentration of dissolved oxygen comprises reducing the dissolved oxygen to the second concentration in the aqueous mixture in the channel and/or the microcompartments in less than or equal to about 30 minutes after the mixture is formed.

Sample material can be deposited into the channel and/or the microcompartments in a variety of ways that are known in the art. This can be done, for example, by pipetting liquid sample material into the channel; by contacting the channel, or an aqueous material therein, with a swab that was used to obtain the sample material (e.g., by swabbing a surface); or by contacting the channel, or an aqueous material therein, with an inoculating loop or needle. After the sample is deposited and the culture device is sealed, the oxygen-scavenging reagent depletes the dissolved oxygen in the device.

EXEMPLARY EMBODIMENTS

Embodiment A is a device, comprising:
a body comprising a waterproof base, a waterproof coversheet attached to the waterproof base, and a channel disposed therebetween, the channel having a perimeter and a sealable opening that provides liquid access to the channel;
  wherein a portion of the perimeter is defined by a waterproof seal; and
a dry first oxygen-scavenging reagent disposed in the device between the base and the coversheet, and
  wherein the waterproof base comprises a plurality of open microcompartment structures facing the coversheet.

Embodiment B is the device of Embodiment A, further comprising an indicator reagent for detecting sulfate reduction by a sulfate-reducing bacterium, wherein the indicator reagent is disposed in the device between the base and the coversheet.

Embodiment C is the device Embodiment B, wherein the indicator reagent is disposed in the device adhered to the waterproof base or the waterproof coversheet.

Embodiment D is the device of Embodiment B or Embodiment C, wherein the indicator reagent is the first oxygen-scavenging reagent.

Embodiment E is the device of device of any one of the preceding Embodiments, wherein the first oxygen-scavenging reagent is disposed in the device adhered to the waterproof base or the waterproof coversheet.

Embodiment F is the device of any one of the preceding Embodiments, further comprising a dry culture medium component disposed in the device between the coversheet and the base, the culture medium component selected to facilitate growth of a sulfate-reducing bacterium.

Embodiment G is the culture device of Embodiment F, wherein the culture medium component comprises an organic carbon source.

Embodiment H is the device of Embodiment G, wherein the organic carbon source is nonfermentable.

Embodiment I is the device of any one of the preceding Embodiments, further comprising a dry second oxygen-scavenging reagent disposed in the device between the coversheet and the base.

Embodiment J is the device of Embodiment I, wherein the second oxygen-scavenging reagent is disposed in the device adhered to the waterproof base or the waterproof coversheet.

Embodiment K is the device of any one of the preceding Embodiments, further comprising a reducing agent.

Embodiment L is the device of Embodiment K, wherein the reducing agent is selected from the group consisting of dithiothreitol, dithioerythritol, a salt of thioglycollic acid, 2-mercaptoethanol and a combination of any two or more of the foregoing.

Embodiment M is the device of any one of the preceding Embodiments,
  wherein the waterproof base has a first adhesive layer disposed thereon facing the coversheet;
  wherein a first dry component is adhered to the first adhesive layer;

wherein the first dry component is selected from the group consisting of the first oxygen-scavenging reagent, the second oxygen-scavenging reagent, the reducing agent, the indicator reagent, the culture medium component, and a combination of any two or more of the foregoing first dry components.

Embodiment N is the device of any one of the preceding Embodiments,
wherein the waterproof coversheet has a second adhesive layer disposed thereon in at least a portion of the channel;
wherein a second dry component is adhered to the second adhesive layer;
wherein the second dry component is selected from the group consisting of the first oxygen-scavenging reagent, the second oxygen-scavenging reagent, the reducing agent, the indicator reagent, the culture medium component, and a combination of any two or more of the foregoing second dry components.

Embodiment O is the device of any one of the preceding Embodiments, wherein the first oxygen-scavenging reagent is water-soluble.

Embodiment P is the device of any one of the preceding Embodiments, wherein the first oxygen-scavenging reagent is selected from the group consisting of ferrous ammonium sulfate, ferrous chloride, ferrous sulfate, a ferrous iron salt, a metal sulfite, and a metal bisulfate.

Embodiment Q is the device of any one of the preceding Embodiments, wherein the second oxygen-scavenging reagent is water-soluble.

Embodiment R is the device of any one of the preceding Embodiments, wherein the second oxygen-scavenging reagent is selected from the group consisting of ascorbic acid and salts thereof.

Embodiment S is the device of any one of the preceding Embodiments, wherein the waterproof seal comprises an adhesive.

Embodiment T is the device of Embodiment S, wherein the adhesive comprises a pressure-sensitive adhesive.

Embodiment U is the device of any one of the preceding Embodiments, wherein the inner surface of the coversheet is substantially flat.

Embodiment V is a method, comprising:
depositing a sample into the channel of the device of any one of the preceding claims;
isolating portions of the sample in a plurality of the microcompartments of the device;
incubating the device at a temperature that facilitates growth of a sulfate-reducing microorganism for a period of time sufficient to detect an indication of a presence of the sulfate-reducing microorganism in at least one of the microcompartments; and
detecting the indication in at least one of the microcompartments or detecting an absence of the indication in all of the microcompartments of the culture device.

Embodiment W is the method of Embodiment V, further comprising depositing an aqueous liquid into the channel.

Embodiment X is the method of Embodiment W, wherein the sample is disposed in the aqueous liquid.

Embodiment Y is the method of Embodiment W or Embodiment X, wherein depositing the aqueous liquid into the channel comprises depositing a predetermined volume of the aqueous liquid.

Embodiment Z is the method of Embodiment Y, wherein depositing a predetermined volume comprises depositing about 1 mL to about 200 mL.

Embodiment AA is the method of any one of Embodiments V through Z, wherein the method further comprises sealing the opening.

Embodiment AB is the method of any one of Embodiments V through AA, wherein incubating the device includes incubating the device for a period 7 days or less.

Embodiment AC is the method of Embodiment AB, wherein incubating the device includes incubating the device for a period 96 hours or less.

Embodiment AD is the method of Embodiment AC, wherein incubating the device includes incubating the device for a period 72 hours or less.

Embodiment AE is the method of Embodiment AD, wherein incubating the device includes incubating the device for a period 48 hours or less.

Embodiment AF is the method of Embodiment AE, wherein incubating the device includes incubating the device for a period 24 hours or less.

Objects and advantages of this invention are further illustrated by the following examples, but the particular materials and amounts thereof recited in these examples, as well as other conditions and details, should not be construed to unduly limit this invention.

EXAMPLES

Example 1: Culture Device Construction

Disposable trays (Quanti-Tray® devices) comprising 51 microcompartments (wells) are obtained from IDEXX Laboratories (Westbrook, Me.). Powder components (i.e., calcium lactate, yeast extract, ascorbic acid, sodium thioglycollate, sodium chloride and ferrous sulfate) of agar-free Medium 2 (J. R. Postgate; "Versatile medium for the Enumeration of Sulfate-Reducing Bacteria"; Appl Microbiol., volume 11, pp. 265-267; which is incorporated herein by reference in its entirety) are blended in quantities sufficient to prepare 100 mL of aqueous medium, with the exception that the quantity of first oxygen scavenger (i.e., ascorbic acid) is adjusted to provide a final concentration of 100 mg/100 mL of aqueous medium. The blended powders are placed into the channel of each of the devices.

Example 2: Alternative Culture Device Construction I—Powder Components Adhered to the Base The disposable trays are obtained as described in Example 1. A thin layer of adhesive (e.g., the copolymer adhesive (without the dye and the antibiotics) described in Example 1 of U.S. Pat. No. 5,089,413; which is incorporated herein by reference in its entirety) is distributed into the bottom of each microcompartment and the solvent is removed by evaporation. The powdered Medium 2 is prepared as described in Example 1. Approximately-equal portions of the powdered medium are distributed onto the adhesive layer in each of the microcompartments.

Example 3: Alternative Culture Device Construction II—Powder Components Adhered to the Coversheet The disposable trays are obtained as described in Example 1. A thin layer of adhesive (e.g., the copolymer adhesive (without the dye and the antibiotics) described in Example 1 of U.S. Pat. No. 5,089,413; which is incorporated herein by reference in its entirety) is spread onto the inside surface (e.g., the surface facing the microcompartments) of the coversheet and the solvent is removed by evaporation. The powdered Medium 2 is prepared as described in Example 1 and is distributed onto the adhesive layer.

Example 4: Detection of Sulfate-Reducing Bacteria in the Culture Devices

ATCC *Desulfovibrio* Medium 2755 is inoculated with an isolated colony of *Desulfovibrio desulfuricans* and is incubated in an anaerobic atmosphere at 30 degrees C. for 5 days. The resulting bacterial suspension is serially-diluted (10-fold dilutions) in $N_2$-sparged 0.1 M phosphate buffer. One-milliliter aliquots of each dilution is mixed with 99 milliliters of sterile water and the resulting mixtures are used to inoculate (via pipet) each of the devices described in Examples 1-3. The devices are heat-sealed using a Quanti-Tray® sealer (IDEXX Laboratories) and the sealed devices are incubated for 7 days at 30 degrees C. After the incubation period, the individual microcompartments are visually inspected for the presence of a black precipitate that indicates presence of sulfate-reducing bacteria in the microcompartment. For each device, the number of compartments containing sulfate-reducing bacteria are recorded and the Most Probable Number (MPN) of sulfate-reducing bacteria in the 1-milliliter sample used to inoculate the device is estimated using the Most Probable Number Table provided by IDEXX Laboratories for use with the Quanti-Tray® devices.

The complete disclosure of all patents, patent applications, and publications, and electronically available material cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

Various modifications may be made without departing from the spirit and scope of the invention. These and other embodiments are within the scope of the following claims.

The invention claimed is:

1. A device, comprising:
a body comprising a waterproof base, a waterproof coversheet attached to the waterproof base, and a channel disposed therebetween, the channel having a perimeter and a sealable opening that provides liquid access to the channel;
wherein a portion of the perimeter is defined by a waterproof seal; and
a dry first oxygen-scavenging reagent and an indicator reagent for detecting sulfate reduction by a sulfate-reducing bacterium are disposed in the device between the base and the coversheet;
wherein the waterproof base comprises a plurality of open microcompartment structures facing the coversheet.

2. The device of claim 1, wherein the indicator reagent is disposed in the device adhered to the waterproof base or the waterproof coversheet.

3. The device of claim 1, wherein the indicator reagent is the first a second oxygen-scavenging reagent.

4. The device of claim 1, wherein the first oxygen-scavenging reagent is disposed in the device adhered to the waterproof base or the waterproof coversheet.

5. The device of claim 1, further comprising a dry culture medium component disposed in the device between the base and the coversheet, the culture medium component selected to facilitate growth of a sulfate-reducing bacterium.

6. The device of claim 5, wherein the culture medium component comprises an organic carbon source.

7. The device of claim 6, wherein the organic carbon source is nonfermentable.

8. The device of claim 1, further comprising a dry second oxygen-scavenging reagent disposed in the device between the base and the coversheet.

9. The device of claim 8, wherein the second oxygen-scavenging reagent is disposed in the device adhered to the waterproof base or the waterproof coversheet.

10. The device of claim 1, further comprising a reducing agent.

11. The device of claim 1;
wherein the waterproof base comprises a first adhesive layer disposed thereon facing the coversheet;
wherein a first dry component is adhered to the first adhesive layer;
wherein the first dry component is selected from the group consisting of the first oxygen-scavenging reagent, a second oxygen-scavenging reagent, a reducing agent, the indicator reagent, a culture medium component, and a combination of any two or more of the foregoing first dry components.

12. The device of claim 11;
wherein the waterproof coversheet comprises a second adhesive layer disposed thereon facing the base;
wherein a second dry component is adhered to the second adhesive layer;
wherein the second dry component is selected from the group consisting of the first oxygen-scavenging reagent, the second oxygen-scavenging reagent, the reducing agent, the indicator reagent, the culture medium component, and a combination of any two or more of the foregoing second dry components.

13. The device of claim 1, wherein the first oxygen-scavenging reagent is water-soluble.

14. The device of claim 1, wherein the first oxygen-scavenging reagent is selected from the group consisting of ferrous ammonium sulfate, ferrous chloride, ferrous sulfate, a ferrous iron salt, a metal sulfite, and a metal bisulfite.

15. The device of claim 8, wherein the second oxygen-scavenging reagent is selected from the group consisting of ascorbic acid and salts thereof.

16. A method, comprising:
depositing a sample into the channel of the device of claim 1;
isolating separate portions of the sample into a plurality of the microcompartments, wherein isolating the separate portions comprises bonding the waterproof coversheet to the waterproof base such that a waterproof seal is formed and the separate portions are enclosed in separate microcompartments;
incubating the device for a period of time under conditions that facilitate growth of an anaerobic microorganism; and
detecting an indication of growth of the anaerobic microorganism in at least one of the separate microcompartments.

17. The method of claim 16, further comprising depositing an aqueous liquid into the channel.

18. The method of claim 17, wherein depositing the aqueous liquid into the channel comprises depositing a predetermined volume of the aqueous liquid.

19. The method of claim 18, wherein depositing a predetermined volume comprises depositing about 0.1 mL to about 100 mL.

20. The method of claim 16, wherein the method further comprises sealing the opening.

* * * * *

UNITED STATES PATENT AND TRADEMARK OFFICE
CERTIFICATE OF CORRECTION

PATENT NO. : 11,072,771 B2
APPLICATION NO. : 15/763744
DATED : July 27, 2021
INVENTOR(S) : Brutinel et al.

It is certified that error appears in the above-identified patent and that said Letters Patent is hereby corrected as shown below:

In the Claims

Column 22
Line 2, In Claim 3, delete "the first", before "a second".

Signed and Sealed this
Fifteenth Day of February, 2022

Drew Hirshfeld
*Performing the Functions and Duties of the*
*Under Secretary of Commerce for Intellectual Property and*
*Director of the United States Patent and Trademark Office*